United States Patent [19]

Karger et al.

[11] Patent Number: 5,665,216

[45] Date of Patent: Sep. 9, 1997

[54] CAPILLARY COLUMN FOR HIGH PERFORMANCE ELECTROPHORETIC SEPARATION AND DETECTION OF SDS PROTEINS AND SYSTEM AND USING THE SAME

[75] Inventors: Barry L. Karger, Newton; Katalin Ganzler, Melrose; Aharon S. Cohen, Brookline, all of Mass.

[73] Assignee: Northeastern University, Boston, Mass.

[21] Appl. No.: 774,044

[22] Filed: Oct. 7, 1991

Related U.S. Application Data

[63] Continuation-in-part of Ser. No. 421,609, Oct. 19, 1989, Pat. No. 5,112,460, which is a continuation-in-part of Ser. No. 359,728, May 19, 1989, abandoned, which is a continuation of Ser. No. 921,311, Oct. 21, 1986, Pat. No. 4,865,706.

[51] Int. Cl.⁶ .................. G01N 27/26; G01N 27/447
[52] U.S. Cl. ............................. 204/605; 204/455
[58] Field of Search ..................... 204/180.1, 299 R, 204/182.8

[56] References Cited

U.S. PATENT DOCUMENTS

| | | | |
|---|---|---|---|
| 2,748,074 | 5/1956 | Davis et al. | 204/606 |
| 3,616,457 | 10/1971 | Hjerten | 204/615 |
| 3,691,054 | 9/1972 | Cawley | 204/616 |
| 3,728,145 | 4/1973 | Hjerten | 204/600 |
| 3,783,118 | 1/1974 | Hjerten | 204/462 |

(List continued on next page.)

FOREIGN PATENT DOCUMENTS

| | | |
|---|---|---|
| 0 272 925 | 6/1988 | European Pat. Off. . |
| 0417925 | 3/1991 | European Pat. Off. . |
| 1233907 | 6/1971 | United Kingdom . |
| WO91/02244 | 2/1991 | WIPO . |
| WO91/11709 | 8/1991 | WIPO . |

OTHER PUBLICATIONS

Allen & Lack, "Standardization in Isoelectric Focusing" in New Directions in Electrophoretic Methods, No Month Available (1987), pp. 117–119.

Chrambach & Bocek, *Trends in Anal. Chem.*, 4, 224 No Month Available (1985).

Giddings, *Separation Science*, 4, 181–189 No Month Available (1969).

Hjerten, *Chromatographic Reviews*, 9, 122–219 No Month Available (1967).

Hjerten, *J. Chromatography*, 270, 1–6 No Month Available (1983).

(List continued on next page.)

*Primary Examiner*—Kathryn L. Gorgos
*Assistant Examiner*—John S. Starsiak, Jr.
*Attorney, Agent, or Firm*—Weingarten, Schurgin, Gagnebin & Hayes LLP

[57] ABSTRACT

A capillary column for high performance electrophoretic separation and detection of SDS proteins and system for using the same is disclosed. A preferred column includes a capillary, a static or dynamic layer of coating material on the inner surface of the capillary wall, and a hydrophilic polymer network which is UV-transparent in the tube, filling it. The capillary column is particularly useful in any electrophoresis system requiring UV-transparent materials.

7 Claims, 11 Drawing Sheets

U.S. PATENT DOCUMENTS

| Patent # | Date | Inventor | Class |
|---|---|---|---|
| 3,876,775 | 4/1975 | Izaka et al. | 514/21 |
| 3,956,273 | 5/1976 | Guiseley | 536/120 |
| 4,118,481 | 10/1978 | Schnabel et al. | 514/12 |
| 4,132,769 | 1/1979 | Osther | 424/174.1 |
| 4,139,346 | 2/1979 | Rabbani | 422/56 |
| 4,152,410 | 5/1979 | Ishiii | 435/7.25 |
| 4,204,929 | 5/1980 | Bier | 204/518 |
| 4,205,129 | 5/1980 | Podolsky et al. | 435/193 |
| 4,275,196 | 6/1981 | Shainoff | 536/115 |
| 4,279,724 | 7/1981 | Hearn et al. | 204/610 |
| 4,284,491 | 8/1981 | Vesterberg | 204/606 |
| 4,290,911 | 9/1981 | Cook et al. | 252/315.3 X |
| 4,312,727 | 1/1982 | Shainoff | 204/469 |
| 4,312,739 | 1/1982 | Hansson et al. | 204/469 |
| 4,319,975 | 3/1982 | Cook | 204/469 |
| 4,319,976 | 3/1982 | Gurske | 204/469 |
| 4,321,121 | 3/1982 | Gurske | 204/469 |
| 4,338,396 | 7/1982 | Kinyasu | 435/17 |
| 4,358,358 | 11/1982 | Rhodes | 435/285.2 |
| 4,362,612 | 12/1982 | Bier | 204/627 |
| 4,415,428 | 11/1983 | Nochumson et al. | 204/606 |
| 4,415,655 | 11/1983 | de Castro et al. | 435/17 |
| 4,427,658 | 1/1984 | Maubois et al. | 514/2 |
| 4,442,655 | 4/1984 | Stroetmann | 53/428 |
| 4,443,427 | 4/1984 | Reinherz et al. | 424/154.1 X |
| 4,451,446 | 5/1984 | Vandevelde et al. | 424/197.11 |
| 4,460,694 | 7/1984 | Fletcher | 436/531 |
| 4,461,833 | 7/1984 | Gordon | 435/183 |
| 4,471,058 | 9/1984 | Smith et al. | 436/518 X |
| 4,481,094 | 11/1984 | de Castro | 204/468 |
| 4,503,147 | 3/1985 | Nakajima et al. | 435/25 |
| 4,512,896 | 4/1985 | Gershoni | 210/635 |
| 4,533,307 | 8/1985 | Ansorge | 425/90 |
| 4,548,869 | 10/1985 | Ogawa et al. | 428/474.7 X |
| 4,548,870 | 10/1985 | Ogawa et al. | 428/474.7 X |
| 4,579,783 | 4/1986 | Ogawa et al. | 428/475.2 X |
| 4,582,868 | 4/1986 | Ogawa et al. | 524/211 X |
| 4,588,492 | 5/1986 | Bier | 204/629 |
| 4,600,641 | 7/1986 | Ogawa et al. | 428/355 X |
| 4,613,459 | 9/1986 | Cantor et al. | 530/351 |
| 4,640,759 | 2/1987 | Hashiue et al. | 204/618 |
| 4,650,556 | 3/1987 | Hashiue et al. | 204/466 |
| 4,650,674 | 3/1987 | Aggarwal et al. | 424/85.5 |
| 4,657,656 | 4/1987 | Ogawa | 204/469 |
| 4,665,164 | 5/1987 | Pernemalm et al. | 536/120 |
| 4,666,829 | 5/1987 | Glenner et al. | 435/6 |
| 4,668,359 | 5/1987 | Postle et al. | 204/606 |
| 4,680,201 | 7/1987 | Hjerten | 427/230 X |
| 4,690,749 | 9/1987 | Van Alstine et al. | 204/454 |
| 4,699,705 | 10/1987 | Ogawa et al. | 204/469 |
| 4,725,343 | 2/1988 | Hjerten et al. | 204/548 |
| 4,747,919 | 5/1988 | Anderson | 204/455 |
| 4,865,706 | 9/1989 | Karger et al. | 204/605 X |
| 4,865,707 | 9/1989 | Karger | 204/453 |
| 5,089,103 | 2/1992 | Swedberg | 204/605 |
| 5,089,111 | 2/1992 | Zhu et al. | 204/451 |

OTHER PUBLICATIONS

Hjerten, *J. Chromatography*, 347, 191–198 No Month Available (1985).

Hames, B.O. & Richwood, D., eds., "Gel Electrophoresis of Proteins", IRL Press, Oxford & Washington, D.C., No Month Available (1981).

Jorgenson, "Electrophoresis", *Anal. Chem.*, 58(7), No Month Available (1986).

Jorgenson & Lukacs, *Anal. Chem.* 53, 1298 No Month Available (1981).

Jorgenson & Lukacs, *Clin. Chem.*, 27, 1551, No Month Available (1981).

Jorgenson & Lukacs, *Science*, 222, 266–272, No Month Available (1983).

Laemmli, *Nature*, 277, 680, No Month Available (1970).

Lederer, M., J. *J. Chromatog.* 390, 468, No Month Available (1987).

Munknes Swank, *Anal. Biochem.*, 39, 462, No Month Available (1971) No Date Available.

Postel et al., *J. Electrophoresis*, 6, 599, No Month Available (1985).

Radola, in *Electrophoretic Techniques*, London: Academic Press, p. 101–104 No Date Available.

Radola, "Rehydratable Polyacryl Gels" in *New Directions in Electrophoretic Methods*, 1987, pp. 68–69.

Tanaka, *Polymer*, 20, 1404, No Month Available (1979).

Tegelstrom & Wyoni, *Electrophoresis*, 7, 99, No Month Available (1986).

Terabe, *Anal. Chem.*, 56, 111–113, No Month Available (1984).

Verheggen & Van De Venne, *J. Chromatog.*, 123, 139 No Month Available (1976).

Weber, *J. Biol. Chem.*, 244, 4406, No Month Available (1969) No Date Available.

M.J. Gordon, X. Hung, S.L. Pentaney, Jr., and R.N. Zare, *Science*, 242, 224, No Month Available (1988).

B.L. Karger, A.S. Cohen and A. Guttman, *J. Chromatog.*, 492, 585, No Month Available (1989).

"Partitioning and Electrophoresis in Flexible Polymer Networks", H. J. Bode, Electrophoresis '79, ©1980 No Month Available Walter de Gruyter & Co., pp. 39–52.

"Electrophoresis of Proteins and Nucleic Acids on Acrylamide–Agarose Gels Lacking Covalent Crosslinking", Horowitz et al, Analytical Biochemistry 143, 333–340 No Month Available (1984).

"The Use of Liquid Polyacrylamide In Electrophoresis", J.J. Bode Analytical Biochemisty 83, pp. 204–210 No Month Available (1977).

"Electrophoresis on uncrosslinked polyacrylamide:Molecular sieving and its potential applications", Tietz et al, Electrophoresis No Month Available 1986, 7, pp. 217–220.

S. Hjertén et al, "High–Performance Electrophoresis of Acidic and Basic Low–Molecular–Weight Compounds and of Proteins in the Presence of Polymers and Neutral Surfactants" Journal of Liquid Chromatography, Marcel Dekker, Inc. 12(13) No Month Available (1989) 2471–2499.

Mingde Zhu et al "Factors Affecting Free Zone Electrophoresis and Isoelectric Focusing in Capillary Electrophoresis" Journal of Chromatography, 480 No Month Available (1989) Elsevier Science Publishers B.V., 311–319.

Hans–Joachim Bode, "The Use of Liquid Polyacrylamide in Electrophoresis I. Mixed Gels Composed of Agar–Agar and Liquid Polyacrylamide" Analytical Biochemistry 83 No Month Available (1977) 204–210.

Hans–Joachim Bode, "The Use of Liquid Polyacrylamide in Electrophoresis II. Relationship between Gel Viscosity and Molecular Sieving" Analytical Biochemistry 83 No Month Available (1977) 364–371.

"SDS—Polyethyleneglycol Electrophoresis: A Possible Alternative to SDS–Polyacrylamide Gel Electrophoresis", Hans–Joachim Bode, North–Holland Publishing Company—Amsterdam, vol. 65, No. 1 May 1976, pp. 56–58.

"Ceric Ion–Initiated Grafting of Acrylonitrile onto Hydrolyzed Cotton", Journal of Applied Polymer Science, vol. 43, 1017–1023 No Month Available (1991).

"High–Performance Capillary of Electrophoresis of Proteins: Sodium Dodecyl Sulphate–Polyacrylamide Gel–Filled Capillary Column for the Determination of Recombinant Biotechnology–Derived Proteins", Kiyoshi Tsuji, Journal of Chromatography, 550 No Month Available (1991) 823–830.

"Short Communication", Alexandra Widhalm, et al, 1991 Elsevier Science Publishers, B.V. Journal of Chromatography, 549 No Month Available (1991) 446–451.

"Separation of DNA Restriction Fragments by High Performance Capillary Electrophoresis with Low and Zero Crosslinked Polyacrylamide Using Continuous and Pulsed Electric Fields", David N. Heiger, et al, 1990 Elsevier Science Publishers, B.V. Journal of Chromatography, 516 No Month Available (1990) 33–48.

CAPILLARY COLUMN FOR HIGH PERFORMANCE ELECTROPHORETIC SEPARATION AND DETECTION OF SDS PROTEINS AND SYSTEM AND USING THE SAME

CROSS-REFERENCE TO RELATED APPLICATIONS

This is a continuation-in-part of application Ser. No. 07/421,609, filed on Oct. 13, 1989, now U.S. Pat. No. 5,112,460 which is a continuation-in-part of application Ser. No. 07/359,728, filed May 31, 1989 now abandoned. Application Ser. No. 07/359,728 is a continuation of parent application Ser. No. 06/921,311, filed Oct. 21, 1986, now U.S. Pat. No. 4,865,706.

FIELD OF THE INVENTION

This invention relates to electrophoresis, and more particularly, to capillary columns containing a polymer network for high performance capillary electrophoresis.

BACKGROUND OF THE INVENTION

Electrophoresis is one of the most widely used separation techniques in the biologically-related sciences. Molecular species such as peptides, proteins, and oligonucleotides are separated by causing them to migrate in a buffer solution under the influence of an electric field. This buffer solution normally is used in conjunction with a low to moderate concentration of an appropriate gelling agent such as agarose or polyacrylamide to minimize the occurrence of convective mixing.

Two primary separating mechanisms exist, separations based on differences in the effective charge of the analytes, and separations based on molecular size. The first of these mechanisms is limited to low or moderate molecular weight materials in the case of separations of oligonucleotides because in the high molecular weight range the effective charges of these materials become rather similar, making it difficult or impossible to separate them. In the case of proteins, charge and size can be used independently to achieve separations. Separations based on molecular size are generally referred to as molecular sieving and are carried out employing as the separating medium gel matrices having controlled pore sizes. In such separating systems, if the effective charges of the analytes are the same, the separation results from differences in the abilities of the different sized molecular species to penetrate through the gel matrix. Smaller molecules move relatively more quickly than larger ones through a gel of a given pore size. Oligonucleotides and medium to high molecular weight polypeptides and proteins are commonly separated by molecular sieving electrophoresis. In the case of proteinaceous materials, however, it is first generally necessary to modify the materials to be separated so that they all have the same effective charges. This is commonly done by employing an SDS derivatization procedure, such as is discussed in "Gel Electrophoresis of Proteins," B. D. Hames and D. Rickwood, Eds., published by IRL Press, Oxford and Washington, D.C., 1981. The contents of this book are hereby incorporated herein by reference.

Sometimes it is desirable to separate proteinaceous materials under conditions which pose a minimal risk of denaturation. In such cases, system additives such as urea and SDS are avoided, and the resulting separations are based on differences in both the molecular sizes and charges.

Most electrophoretic separations are today conducted in slabs or open beds. However, such separations are hard to automate or quantitate. Extremely high resolution separations of materials having different effective charges have been achieved by open tubular free-zone electrophoresis and isotachophoresis in narrow capillary tubes. In addition, bulk flow can be driven by electroosmosis to yield very sharp peaks. Such high efficiency open tubular electrophoresis has not generally been applied to the separation of medium to high molecular weight oligonucleotides, however, since these materials have very similar effective charges, as indicated above. In addition, open tubular electrophoresis does not provide size selectivity for proteinaceous materials.

Hjerten has published an article in the *Journal of Chromatography*, 270, 1–6 (1983), entitled "High Performance Electrophoresis: The Electrophoretic Counterpart of High Performance Liquid Chromatography," in which he employs a crosslinked polyacrylamide gel in tubes having inside dimensions of 50–300 micrometers, and wall thicknesses of 100–200 micrometers. However, this work suffers from limited efficiency and relatively poor performance due in part to the use of relatively wide bore capillaries, relatively low applied fields, high electrical currents, and insufficient suppression of electroendosmosis. He has also obtained U.S. Pat. No. 3,728,145, in which he discloses a method for coating the inner wall of a large bore tube with a neutral hydrophilic substance such as methyl cellulose or polyacrylamide to reduce electroendosmosis in free-zone electrophoresis in open tubes. In a later patent, U.S. Pat. No. 4,680,201, Hjerten discloses a method for coating the inner wall of a narrow bore capillary with a monomolecular polymeric coating of polyacrylamide bonded to the capillary wall by means of a bifunctional reagent. These capillaries are also open tubes to be used for free-zone electrophoresis.

The work in the field of electrophoresis in capillaries by researchers other than the present applicants has generally resulted in polyacrylamide columns which were not highly stable and could not be subjected to sufficiently high electric fields to achieve high efficiencies and high resolution separations. Improved capillary columns containing a polyacrylamide polymer network for electrophoresis which provide superior stability, and efficiency, have been disclosed by the present inventors in application Ser. No. 07/421,609, (Batch No. P34), the entire contents of which are hereby incorporated by reference. The capillary columns disclosed in the above mentioned Patent Application are suitable for sodium dodecyl sulfate polyacrylamide gel electrophoresis (SDS-PAGE); however, UV detection of SDS-proteins in polyacrylamide-filled capillaries is strictly limited to a specific wavelength of about 250 nm and higher due to the high UV absorbance associated with polyacrylamide gels, crosslinked or uncrosslinked.

Figure 1:
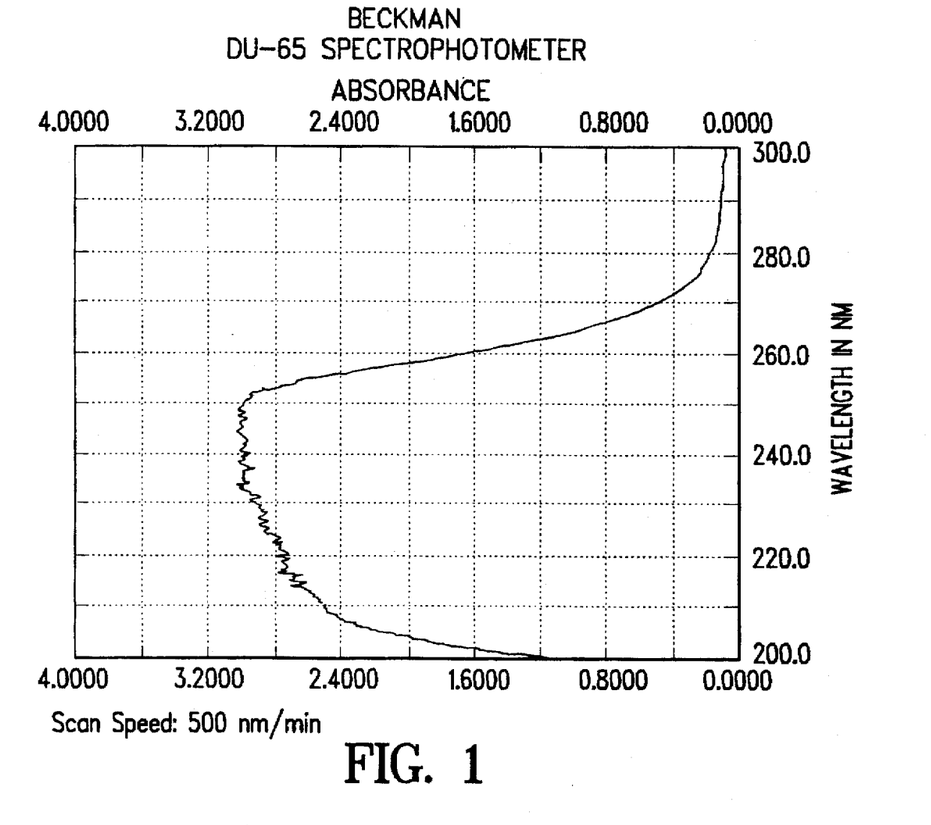
FIG. 1 is a UV spectrum of a 3%T, 0%C polyacrylamide polymer network polymerized in distilled water (scan limits: 200 nm to 300 nm; scan speed 500 nm/min; 4.000 Absorbant Unit Full Scale (A.U.F.S.); optical light path 0.5 cm)

For example, FIG. 1 shows the UV spectra of a 3%T (total monomer) and 0%C (crosslinker) polyacrylamide polymer network polymerized in distilled water. As is seen in FIG. 1, the absorbance is very high at the lower UV range. Moreover, the higher the acrylamide (or bisacrylamide) content of the polymer network, the higher the absorption.

Figure 2:
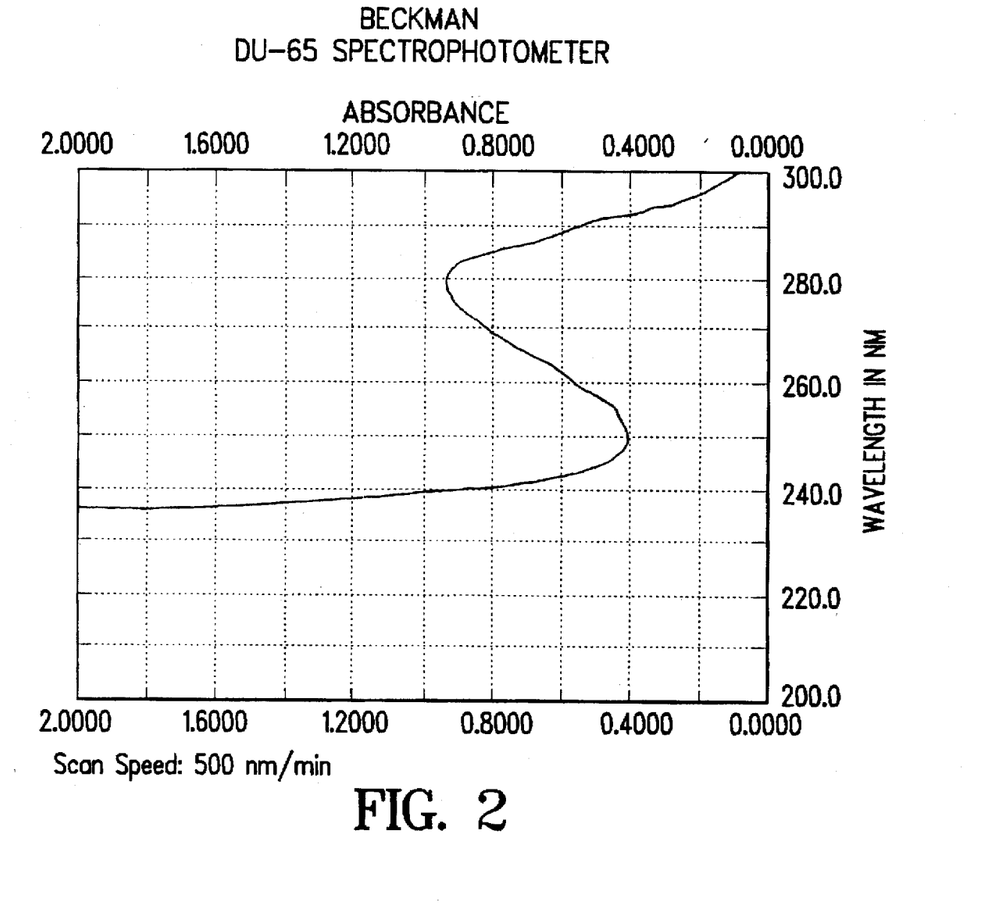
FIG. 2 is a UV spectrum of a 1.5 mg/mL ovalbumin solution (scan limits: 200-300 nm; scan speed 500 nm/min; 2.000 A.U.F.S.; optical light path 0.5 cm)

It is known that proteins intensively absorb at 214 nm due to the peptide bonds. The absorption at 214 nm can be called non-specific, since all peptide bonds absorb at that wavelength, while absorption at 280 nm is restricted to the proteins containing aromatic amino acids. FIG. 2 shows a typical UV spectrum of a protein. As is shown in FIG. 2, the intensity of the absorption at 214 nm is much higher than that at 280 nm.

Therefore, the sensitivity and the selectivity of UV detection would be at its highest if measurements could be taken at 214 nm. However, due to the high absorption of the polyacrylamide-filled capillaries at a wavelength of 214 nm, measurements are instead taken at wavelengths of around 280 nm. Thus, although the polyacrylamide-filled capillaries do not exhibit intense absorption at 280 nm, the selectivity and sensitivity for detecting proteins is very reduced at that wavelength.

Therefore, the sensitivity and selectivity of on-column UV detection of SDS-proteins such as is used in a capillary electrophoresis system could be greatly improved if on-column detection was achieved at lower UV wavelengths.

SUMMARY OF THE INVENTION

The invention relates to a capillary column for high performance electrophoretic separation and high sensitivity detection of SDS-proteins and a system for using the same. The column of the invention includes a capillary, a static or dynamic layer of coating material on the inner surface of the capillary wall, and a hydrophilic polymer network which is UV-transparent in the tube, filling it. The capillary column of the invention is particularly useful in any electrophoresis system requiring UV-transparent materials where the detection of sample is performed on-column, usually by UV detection.

DESCRIPTION OF THE DRAWING

The invention will be more fully understood from the following solely exemplary detailed description taken in conjunction with the accompanying drawings in which.

DETAILED DESCRIPTION OF THE INVENTION

Figure 3:
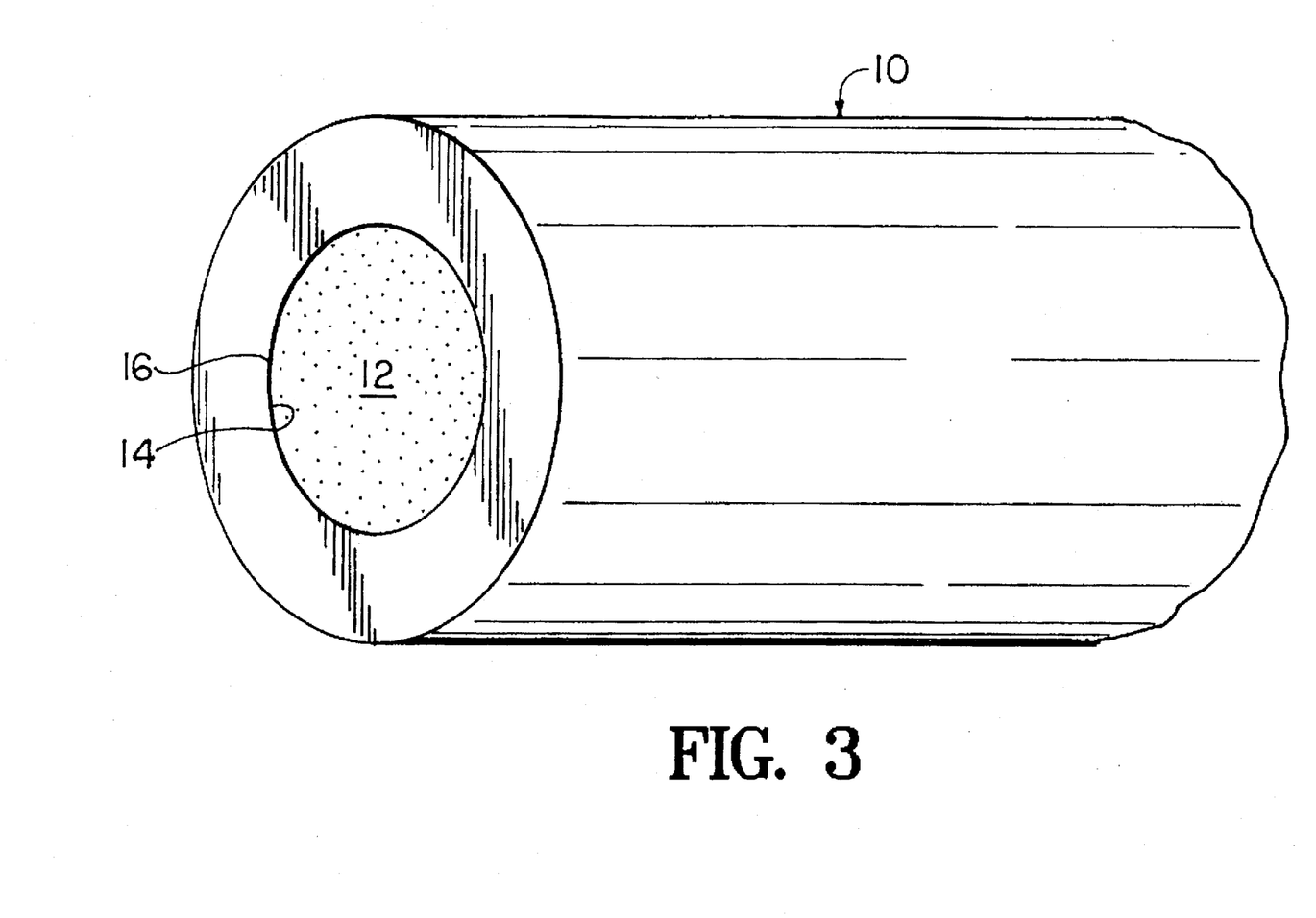
FIG. 3 shows a magnified perspective view of a capillary column filled with a hydrophilic polymer network which is UV-transparent in accordance with the invention.

As shown in FIG. 3, the capillary column of the invention includes a capillary 10, a layer 16 of dynamic or static coating material on the inner surface 14 of the capillary wall, and a UV-transparent hydrophilic polymer network material 16 within the bore of this capillary.

As employed herein, the term "polymer network" encompasses a polymeric gel or polymeric solution and means a three-dimensional network of polymer chains held together by any of a variety of means such as covalently bonded crosslinking units, long range attractive forces, hydrogen bonds, entanglement of the molecular chains, etc., and dispersed in a liquid phase. The polymeric network provides sufficient structure for a degree of rigidity, and other components of the system occupy the spaces between the polymeric chains.

The capillary may be made of any of a variety of materials provided that it is UV-transparent and the detection system to be employed in the electrophoresis can function adequately with the particular material employed. Preferably, the capillary is made of fused silica.

As employed herein, the term "UV-transparent" is defined as having negligible absorbance throughout the UV wavelength range of about 200 nm to 300 nm.

The capillary dimensions are important because, for a given electric field, as the internal diameter of the capillary is reduced, the electric current and the resultant heating produced by a particular applied electric field is reduced. Thus, for highest resolution separations it is desirable that the capillary have a minimum internal diameter. With the improved capillaries of this invention, however, this factor is somewhat less important than formerly. Accordingly, capillaries having internal diameters in the range between 10 and 2000 micrometers function in the invention. A preferred range of internal diameters is 20 to 200 micrometers. A polyimide coating on the outer surface of the capillary permits easy handling of thin-walled microcapillaries.

The polymer network 16 employed can be any hydrophilic polymer which is UV-transparent. Suitable polymers include polyethylene glycol (PEG), polyethylene oxide (PEO), cellulose derivatives, dextran, polyvinyl alcohol, agarose, and modifications or mixtures thereof. The concentration of any of the named polymers in the polymer network ranges from about 2%–30%; however, the upper range may be determined by the highest soluble concentration of any of the named hydrophilic polymers. Furthermore, any of the named polymers may be linear or in uncrosslinked form. The polymer network 16, may optionally include a UV-transparent buffer such as TRIS-CHES, MES-Na, and AMPD-CACO.

In one embodiment, the polymeric network comprises approximately 5%–20% uncrosslinked dextran, and a buffer such as AMPD-CACO. The polymer network may be prepared in accordance with procedures well known in the art of preparing separation media for electrophoresis.

It is preferable when using dextran to coat the inner wall of the capillary with a static coating which functions to reduce electroendoosmosis. Examples of suitable coating materials include but are not limited to those which are disclosed in application Ser. No. 07/421,609 (Batch P34) hereby incorporated by reference.

The coating material may optionally be a dynamic coating material which is capable of reversibly adsorbing to the inner wall of the capillary. An example of a dynamic coating arises when using hydroxy propyl cellulose as a component of the polymer network. The cellulose acts as a dynamic coating to reduce electroendoosmosis as well as comprising a component of the polymer network itself.

The capillary column 10 is used in conjunction with apparatus and techniques which are generally known to those skilled in the art of capillary electrophoresis and which are described in detail in application Ser. No. 07/421,609. For example, the capillary column of the invention may be suitable for use with commercially available automated capillary electrophoresis systems such as the P/ACE (Beckman Instruments).

A sample of SDS-proteins may be injected into the capillary column of the invention by known techniques in the art such as the "electrophoretic injection" technique, syringe layering or pressure injection. The capillary column is then placed in a solution of UV-transparent "running buffer" such as a buffer described above, an electrophoretic field is applied, and the electrophoresis is carried out in the normal way as is known in the art. The sample may be instrumentally detected and measured on-column preferably by UV spectroscopy.

In one embodiment, the electric field may be a pulsed electric field. The series of voltage pulses which result in the pulsed field need not be repetitive, but may be either repetitive or variable and complex. Field pulsing may be applied during selected portions of the electrophoresis run and need not be employed throughout the run. Different combinations of waveforms may be employed during various portions of the electrophoresis run. The times field pulsing is employed can vary in length from one portion of the electrophoresis run to another. Virtually any appropriate combination of pulse shapes, pulse durations, and durations of pulsing in various portions of the electrophoresis run may be employed, to accomplish the desired separations. The particular pulsing conditions best suited for particular separations are experimentally determined.

The capillary column containing the UV-transparent polymer network in accordance with the invention is particularly suitable for use in capillary electrophoresis as the polymer network can be maintained within the capillary column even under harsh electrophoretic conditions such as the use of a wide range of applied electrophoretic fields including relatively high fields of about 50 V/cm to about 1000 V/cm. A cooling system is useful at the high field end. To aid in cooling the capillary, a cooling jacket or a related device is employed around the capillary over most of its length, excluding only the front and the rear ends of the capillary, which are respectively immersed in buffer solution and connected to the detector of the electrophoretic system. A cooling fluid is circulated through this jacket and maintained at whatever temperature is desired. Alternatively, an electrically controlled mechanical cooling device may be employed around the capillary column. Such "active" cooling is more effective in maintaining desired capillary temperatures than forced air or natural convection.

Another important feature of the capillary of the invention is that it may be reused for the separation and detection of numerous consecutive samples. Furthermore, due to the relatively low viscosity of the polymer network contained within the capillary, the capillary may be easily regenerated by blowing the polymer network out of the column without removing the column from the electrophoresis apparatus, and refilling the column with polymer network for subsequent sample analysis. This feature provides an important advantage over a capillary column containing a polymeric gel comprising crosslinked or linear acrylamide above 6% T, as such columns can not be regenerated as easily as the capillary columns of the present invention, and therefore have a shorter lifetime.

Figure 4A:
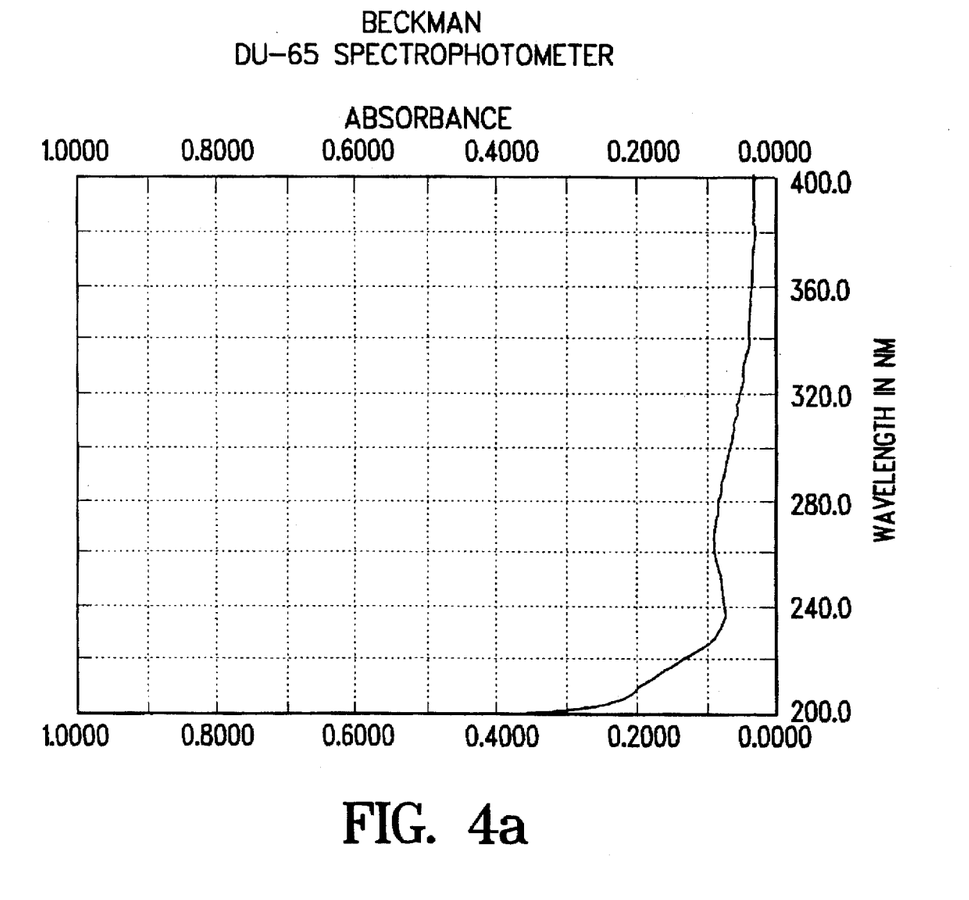
FIG. 4a shows UV spectrum of 20% dextran dissolved in water (MW of dextran 2,000,000), (scan limits: 200 nm to 300 nm; scan speed 500 nm/min; 3.000 A.U.F.S., optical light path 0.5 cm)

Moreover, the capillary containing a UV-transparent polymer network in accordance with the invention is very suitable for the measurement of SDS-proteins at relatively low UV wavelengths of about 214 nm. Detection of SDS-proteins at these wavelengths is much more sensitive and selective than detection at 280 nm. As discussed above, capillary electrophoresis performed with polyacrylamide-filled capillaries is limited to detection at higher UV wavelengths of around 280 nm, due to the high absorbance of the polyacrylamide at low UV wavelengths. FIG. 4a shows the spectrum of a UV-transparent polymer network prepared from a stock solution of 20% dextran dissolved in distilled water. As can be seen in FIG. 4a, the UV absorbance of the polymer network is negligible throughout the entire UV spectrum providing good detectability at 214 nm.

Figure 4B:
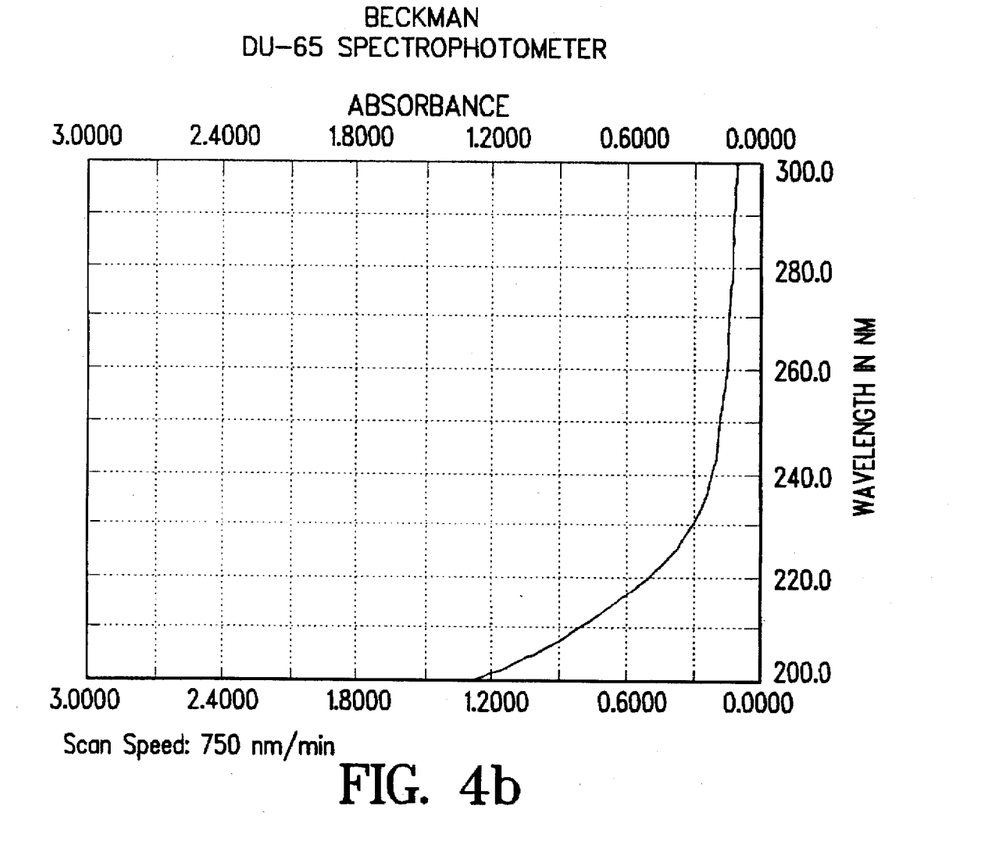
FIG. 4b shows a UV spectrum of 0.5% agarose dissolved in water.
Figure 4C:
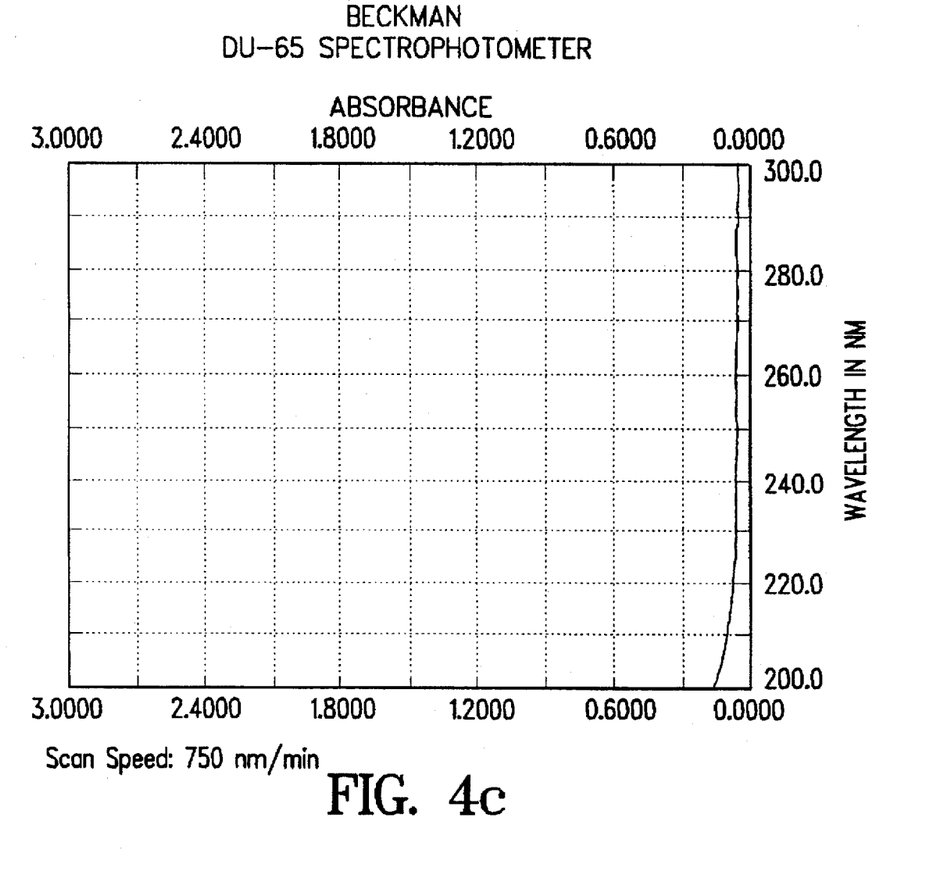
FIG. 4c shows a UV spectrum of 2% polyethylene oxide (PEO) (mw 5,000,000) dissolved in water PEG.
Figure 4D:
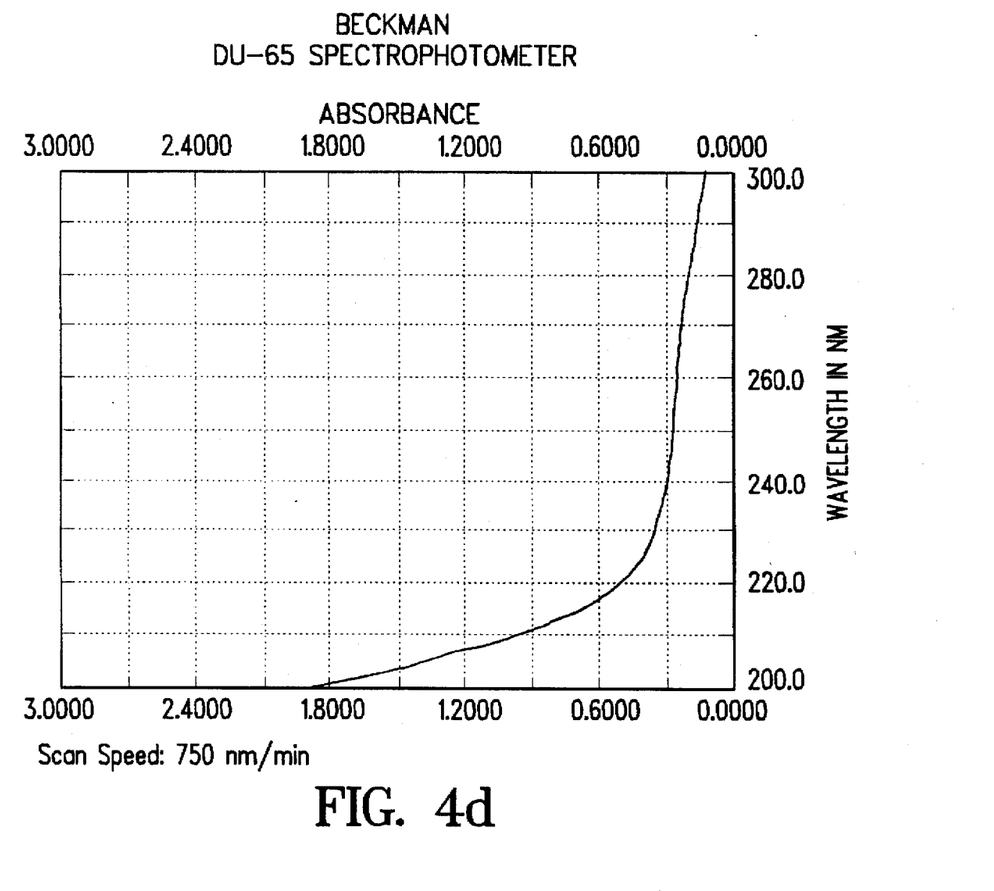
FIG. 4d shows a UV spectrum of 0.25% methylcellulose dissolved in water.

Similarly, FIGS. 4b–4d show that the UV absorbance of PEO, agarose, and methylcellulose, respectively, is minimal throughout the entire UV spectra providing for good detectability at 214 nm.

Figure 5A:
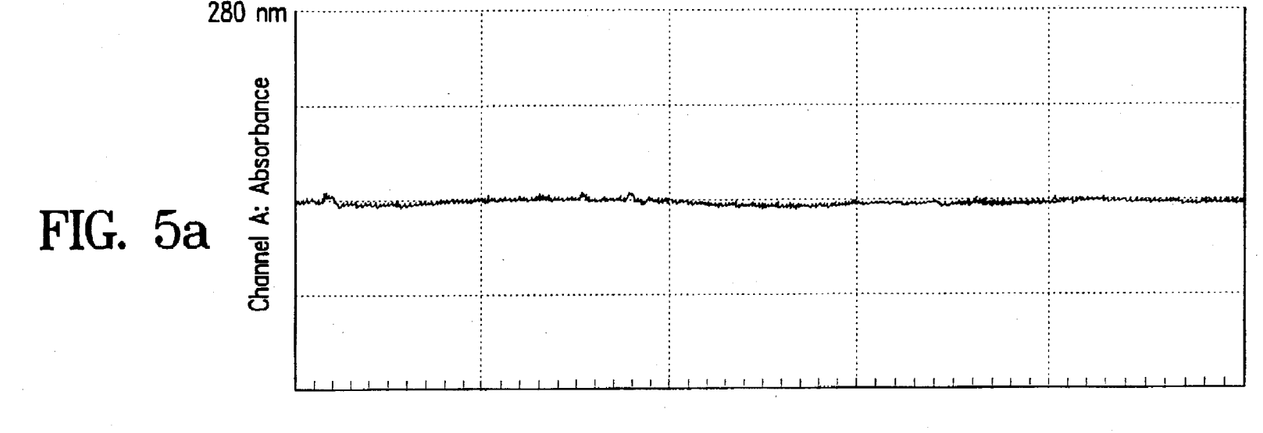
FIG. 5a shows an electropherogram of SDS-protein standards on 10% dextran (mw 2,000,000) (separating buffer: 0.05M 2-amino-2-methyl-1,3-propanediol (AMPD)-cacodylic acid (CACO), 0.1% SDS, pH 8.8; applied field: 200 V/cm; effective length: 17 cm; detection at 280 nm)
Figure 5B:
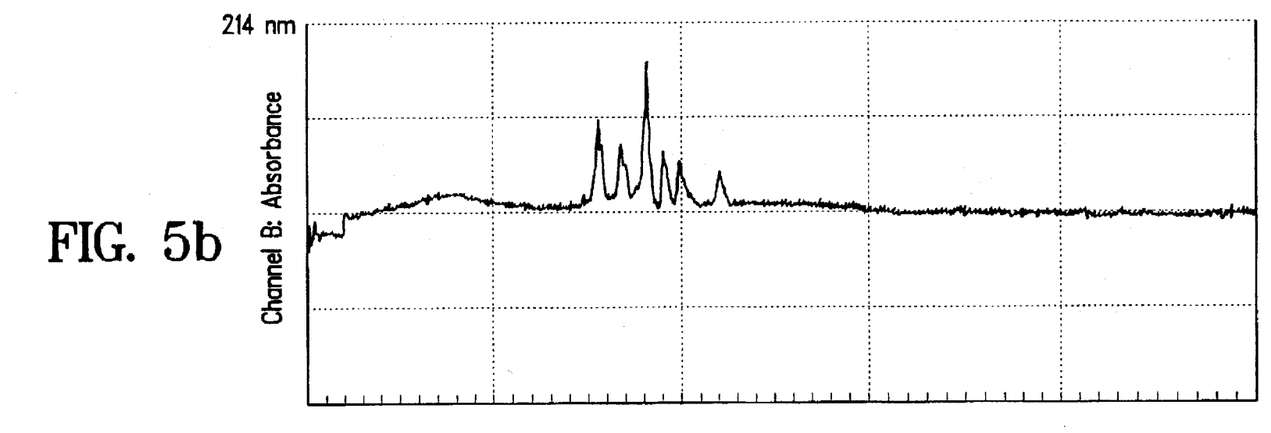
FIG. 5b shows an electropherogram of SDS-protein standards on 10% dextran (all other conditions are the same as those in FIG. 5a except detection is at 214 nm)

FIGS. 5a and 5b show comparative electropherograms of SDS-protein standards in 10% dextran (mw 2,000,000). FIG. 5a shows an electropherogram taken at a wavelength of 280 nm. FIG. 5b shows an electropherogram taken at a wavelength of 214 nm. Detection was performed on-column and all other conditions were the same. As can be seen from comparing the electropherograms, the SDS protein samples were not detected at a wavelength of 280 nm, which is the wavelength generally used to detect SDS proteins using a polyacrylamide polymer network in capillary electrophoresis. By comparison, detection of sample at 214 nm was much more sensitive and selective.

Figure 6:
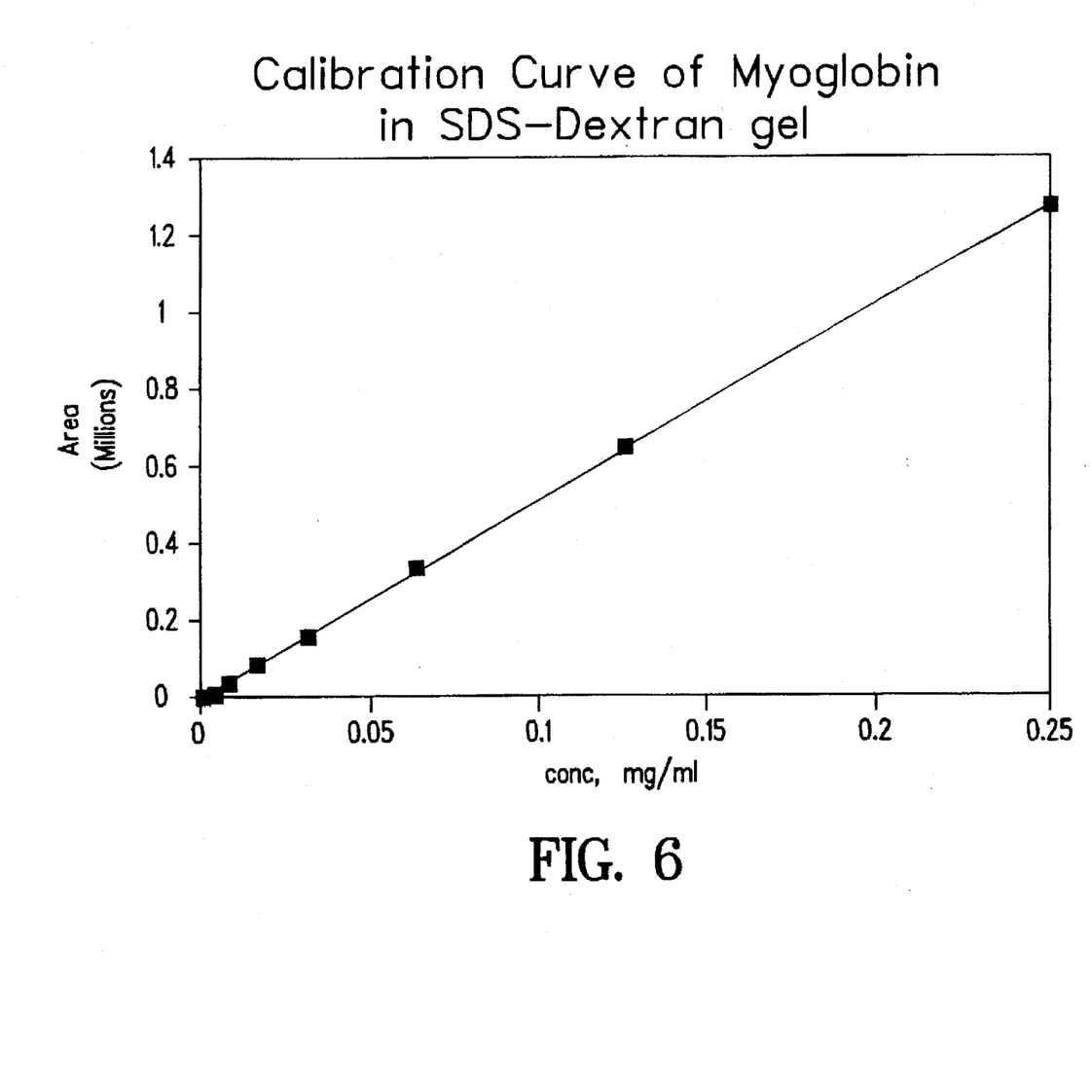
FIG. 6 is a calibration curve of myoglobin on 10% dextran, 0.1% SDS.

Furthermore, a calibration curve of myoglobin in SDS-10% dextran (FIG. 6), exhibits linear behavior through myoglobin concentrations ranging from 0.5 ug/ml to 250 ug/ml. Calibration plots for acrylamide gels do not exhibit linear behavior over such a large concentration range and are therefore, more difficult to use in situations where quantitative analysis is required.

The invention is further illustrated in the following examples.

EXAMPLE #1

A capillary column was first pretreated by coating the inner wall of the capillary with a bifunctional reagent to reduce electroendoosmosis (es). The surface of the capillary was treated with 0.1N NaOH. A 26% (V/V) (3-glycidoxypropyl-trimethoxysilane (Petrarch Systems, Bristol, Pa.) was dissolved in a 65% ethanol, 3% acetic acid solution. The capillary was washed with 300 volumes of the silanizing solution. The capillary was then filled with 6% acrylamide solution. A 0.5% ammonium persulfate and 10% TEMED solution was used to initiate the binding reaction between the acrylamide and the silanized wall. A dextran layer was bound by a free radical reaction using Ce IV ions to the top of the acrylamide layer. This technique is known in the art as "graft polymerization" (see, N. M. Safy El-Din, *J. Appl. Polymer Sci.*, 43, pp. 1017–1023 (1991)). The effectiveness of the coating was checked by measuring the electroosmotic flow. The electroendoosmosis was decreased more than 10 fold in the pretreated capillary as compared to the level of electroendoosmosis in an untreated capillary, and almost no electroosmotic flow was measured.

The separating buffer was prepared from HPLC grade materials used for buffers. The chemicals were all of analytical grade purchased from Sigma (St. Louis) unless otherwise indicated. To detect at the low UV wavelengths, a UV-transparent buffer was chosen. The buffer comprised 0.05M AMPD-CACO and 0.1% SDS dissolved in distilled water. The pH of the buffer was adjusted pH 8.8. The buffer was degassed extensively prior to use by vacuum degassing and He purge.

The UV-transparent polymer network was prepared from a stock solution of dextran (MW of 2,000,000) in the separating AMPD-CACO buffer described above. The polymer network comprised 10% (w/V) dextran. The polymer network solution was carefully degassed as discussed above and was loaded into the pretreated capillary column using a gas tight syringe.

The column was placed on an P/ACE instrument (Beckman Instruments). Five different SDS-protein standards were loaded on the column by pressure injection. The samples were as follows:

| | |
|---|---|
| Sample 1 | myoglobin; |
| Sample 2 | carbonic anhydrase; |
| Sample 3 | ovalbumin; |
| Sample 4 | bovine serum albumin; |
| Sample 5 | phosphorylase 3. |

Figure 7:
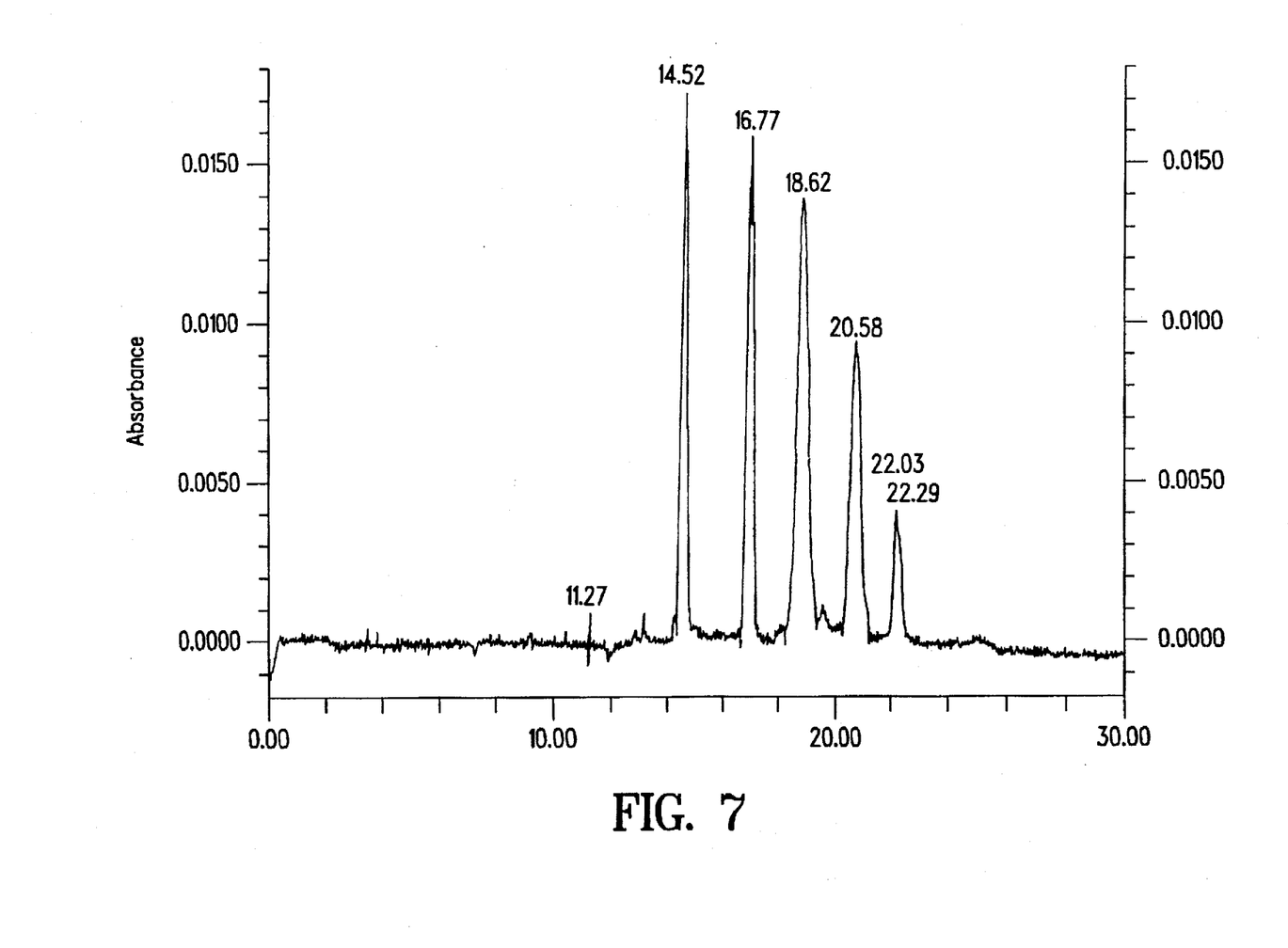
FIG. 7 shows an electropherogram of SDS-protein standards, on 10% dextran (MW 2,000,000) (conditions the same as those in FIG. 5b)

The samples were run in 0.05M AMPD-CACO, 0.1% SDS buffer, pH 8.8, at an applied voltage of 300 V/cm. Detection was at 214 nm, 0.01 A.U.F.S. The resulting electropherogram is shown in FIG. 7.

As can be seen in the electropherogram, the capillary containing UV-transparent polymer network enabled very selective and very sensitive detection of the protein samples at 214 nm which is the ideal UV wavelength for detection of such samples.

EXAMPLE #2

A capillary column containing a 10% dextran polymer network was prepared as described in Example #1.

The UV-transparent separating buffer comprised 0.05M AMPD-CACO, pH 8.8 and 0.1% SDS dissolved in distilled water. The buffer was degassed extensively prior to use using vacuum degassing and He purge.

Figure 8:
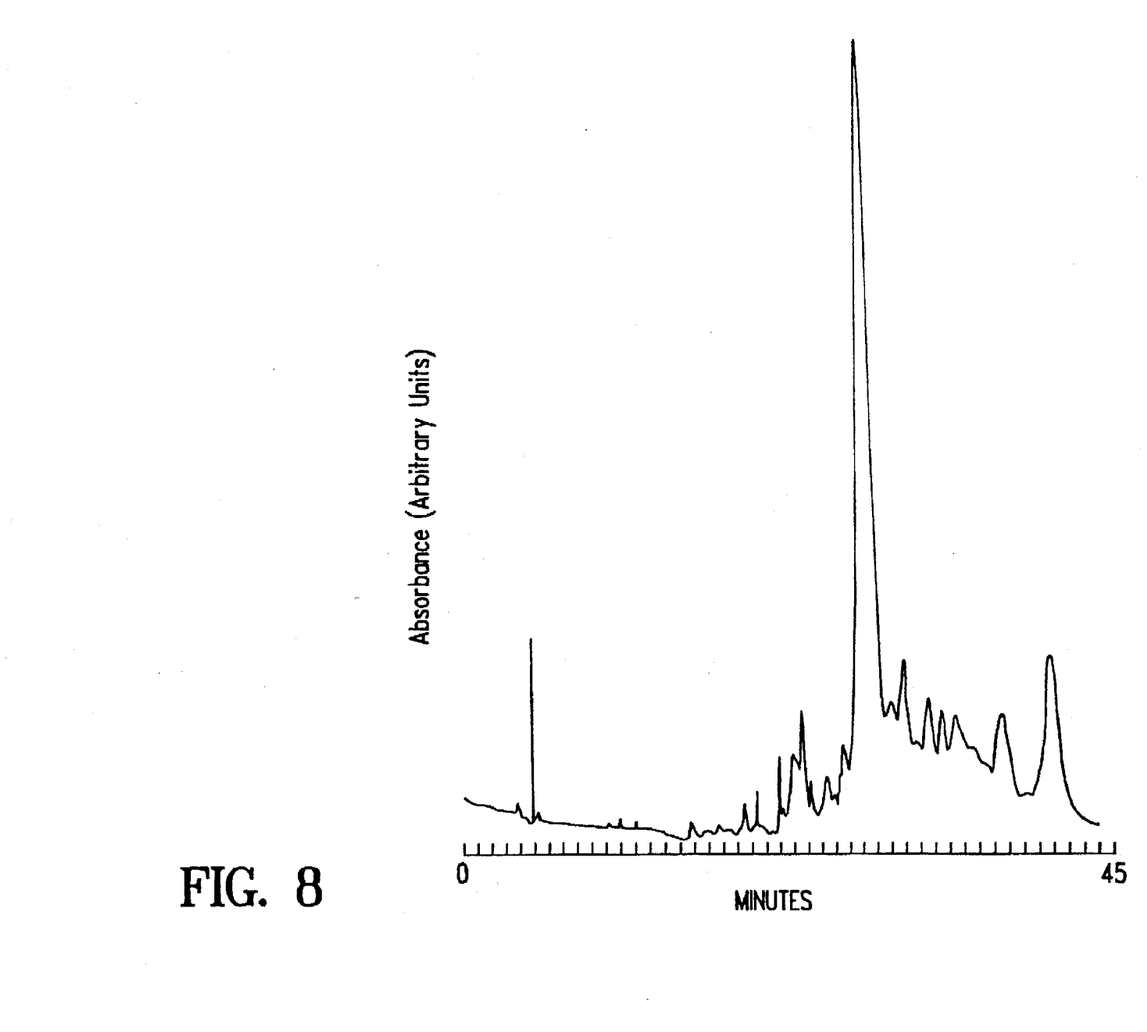
FIG. 8 shows an electropherogram of rat plasma sample on 10% dextran (MW 2,000,000) (separating buffer: 0.05M AMPD-CACO, 0.1% SDS, pH 8.8; applied field: 300 V/cm; effective length: 24 cm; detection at 214 nm)

The column was used in a manual system (Spectra Physics detector). A sample of rat plasma was loaded on the column by electrokinetic injection. The resulting electropherogram is shown in FIG. 8.

As can be seen in the electropherogram, the capillary containing the UV-transparent polymer network enabled very selective and very sensitive separation and detection of the rat plasma sample at 214 nm.

The invention is not to be limited by what has been particularly shown and described except as indicated by the appended claims.

What is claimed is:

1. A capillary column containing a UV-transparent polymer network for high performance electrophoretic separation and high sensitivity detection of SDS-proteins comprising:

a capillary having an interior cavity and a wall with an inner surface;

a layer of coating material on said inner surface of said wall;

a UV-transparent hydrophilic polymer network filling said interior cavity; and a UV-transparent buffer, said buffer being selected from a group consisting of Tris-Ches, MES-Na, and AMPO-cacodylic acid (CACO).

2. The capillary of claim 1 wherein said capillary is made of fused silica.

3. The capillary of claim 1 wherein said UV-transparent hydrophilic polymer is selected from the group consisting of dextran, PEG, PEO, agarose, cellulose derivatives, polyvinyl alcohol and mixtures thereof.

4. The capillary of claim 3 wherein said concentration of salad hydrophilic polymer in said polymer network ranges from about 2% to the highest soluble concentration of the polymer.

5. The capillary of claim 1 wherein said coating material is a dynamic coating material.

6. The capillary of claim 1 wherein said coating material is a static coating material.

7. A capillary column containing a UV-transparent polymer network for high performance electrophoretic separation and high sensitivity detection of SDS-proteins comprising:

a capillary having an interior cavity and a wall with an inner surface;

a layer of coating material on said inner surface of said wall;

a UV-transparent hydrophilic polymer network filling said interior cavity, said polymer network comprising approximately at least 5% dextran; and a UV-transparent buffer, said buffer being selected from a group consisting of Tris-Ches, MES-Na, and AMPO-cacodylic acid (CACO).

* * * * *

UNITED STATES PATENT AND TRADEMARK OFFICE
CERTIFICATE OF CORRECTION

PATENT NO. : 5,665,216
DATED : September 9, 1997
INVENTOR(S) : Karger et al.

It is certified that error appears in the above-identified patent and that said Letters Patent is hereby corrected as shown below:

In the Title: "...AND USING THE SAME", should read --FOR USING THE SAME--.

In Related U.S. Application Data "...May 19, 1989", should read --May 31, 1989--.

Column 1, line 4, "..and using the", should read --for using the--.

Column 8, line 28, "salad hydrophilic", should read --said hydrophilic--.

Signed and Sealed this

Third Day of August, 1999

Attest:

Attesting Officer

Q. TODD DICKINSON

Acting Commissioner of Patents and Trademarks